(12) United States Patent
Claypool et al.

(10) Patent No.: US 8,372,083 B2
(45) Date of Patent: Feb. 12, 2013

(54) SURGICAL INSTRUMENT ADAPTER

(75) Inventors: Jody L. Claypool, Columbia City, IN (US); Robert A. Hodorek, Warsaw, IN (US); Adam M. Griner, Columbia City, IN (US)

(73) Assignee: Zimmer, Inc., Warsaw, IN (US)

( * ) Notice: Subject to any disclaimer, the term of this patent is extended or adjusted under 35 U.S.C. 154(b) by 1388 days.

(21) Appl. No.: 11/643,453

(22) Filed: Dec. 21, 2006

(65) Prior Publication Data

US 2008/0154274 A1   Jun. 26, 2008

(51) Int. Cl.
*A61B 17/90* (2006.01)
(52) U.S. Cl. .......................................................... 606/96
(58) Field of Classification Search ................ 606/86 R, 606/87–89, 96–98
See application file for complete search history.

(56) References Cited

U.S. PATENT DOCUMENTS

| | | | |
|---|---|---|---|
| 5,403,322 A * | 4/1995 | Herzenberg et al. ............ 606/98 |
| 5,683,398 A * | 11/1997 | Carls et al. ...................... 606/89 |
| 5,888,034 A * | 3/1999 | Greenberg ................. 408/115 R |
| 6,342,056 B1 | 1/2002 | Mac-Thiong et al. |
| 6,796,986 B2 * | 9/2004 | Duffner .......................... 606/87 |
| 7,192,432 B2 * | 3/2007 | Wetzler et al. ................... 606/96 |
| 7,278,997 B1 * | 10/2007 | Mueller et al. ................ 606/104 |
| 7,364,581 B2 * | 4/2008 | Michalowicz .................. 606/87 |
| 2002/0198531 A1 * | 12/2002 | Millard et al. ................... 606/87 |
| 2003/0083667 A1 | 5/2003 | Ralph et al. |
| 2007/0276401 A1 * | 11/2007 | Choe et al. ...................... 606/96 |

* cited by examiner

Primary Examiner — Kevin T Truong
Assistant Examiner — Christopher Beccia
(74) Attorney, Agent, or Firm — Schwegman, Lundberg & Woessner, P.A.

(57) ABSTRACT

An adapter to provide moveable configurations of securing structures such as fastener apertures or throughbores for fastening a surgical instrument to an anatomical structure, such as a bone. The adapter is connectable to the surgical instrument in a plurality of discrete locations on the surgical instrument, thereby allowing a surgeon to select an optimum fixation location for fastening the surgical instrument to the anatomical structure. The adapter may be cannulated to accommodate a fastener and may be slidably affixed to the surgical instrument while simultaneously providing stable fixation between the surgical instrument and the bone. The adapter may be configured to mate with another adapter having a similar configuration such that multiple fixation locations may be provided to the surgeon. Moreover, a plurality of adapters may be connected to the surgical instrument either directly or indirectly through another adapter to select multiple optimum fixation locations.

17 Claims, 1 Drawing Sheet

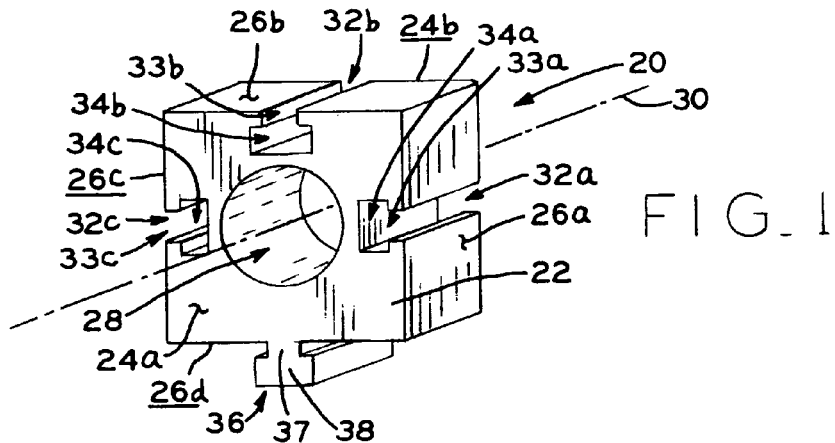
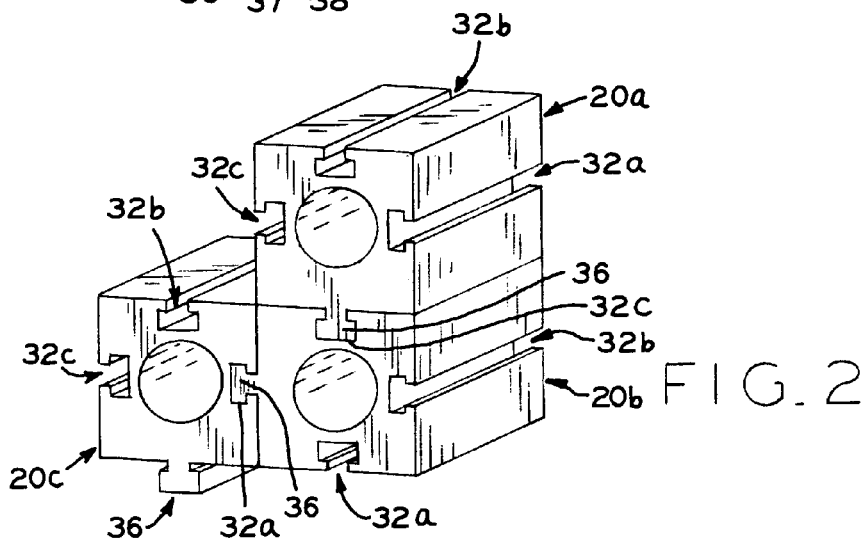
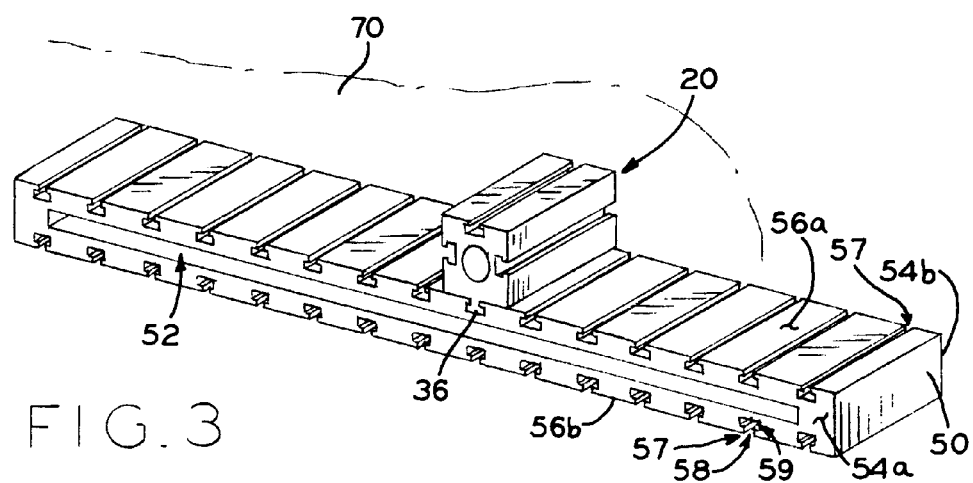

SURGICAL INSTRUMENT ADAPTER

BACKGROUND

1. Field of the Invention

The present invention relates to surgical instruments. More particularly, the present invention relates to surgical instrument adapters providing a plurality of geometrical relationships between a surgical instrument and a fastener used to secure the surgical instrument to an anatomical structure.

2. Description of the Related Art

Typical surgical instruments and tools, such as cut guides, drill guides, and alignment tools, for example, require fixation to an anatomical structure, such as a bone, for example. These instruments may include apertures or throughbores which provide passage for fasteners therethrough for fixating the instrument to the bone. The fastener apertures are generally configured to provide fixation points between the instrument and the bone. The fastener aperture configurations, however, are not movable with respect to the instrument and the anatomical structure. The lack of customization due to the static nature of the fastener aperture configurations of the instruments creates potential access difficulties for a surgeon, particularly in a minimally invasive surgical procedure.

SUMMARY

The present invention provides an adapter to provide moveable configurations of securing structures such as fastener apertures or throughbores for fastening a surgical instrument to an anatomical structure, such as a bone. The adapter is connectable to the surgical instrument in a plurality of discrete locations on the surgical instrument, thereby allowing a surgeon to select an optimum fixation location for fastening the surgical instrument to the anatomical structure. The adapter may be cannulated to accommodate a fastener and may be slidably affixed to the surgical instrument while simultaneously providing stable fixation between the surgical instrument and the bone. The adapter may be configured to mate with another adapter having a similar configuration such that multiple fixation locations may be provided to the surgeon. Moreover, a plurality of adapters may be connected to the surgical instrument either directly or indirectly through another adapter to select multiple optimum fixation locations.

In one form thereof, the present invention provides a surgical device usable with an anatomical structure, including a surgical instrument; and a connector releasably securable to the surgical instrument in a plurality of discrete positions, the connector configured to receive a fastener for connecting the surgical instrument to the anatomical structure.

In another form thereof, the present invention provides a surgical device usable with an anatomical structure, including a surgical instrument; a fastener; and connector means for cooperating with the fastener to connect the surgical instrument to the anatomical structure and for varying a geometrical relationship of the surgical instrument and the fastener.

In yet another form thereof, the present invention provides a method of securing a surgical instrument to an anatomical structure, including the steps of connecting an adapter to the surgical instrument in one of a plurality of connection positions; and fastening the surgical instrument to the anatomical structure through the adapter.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 1 is a perspective view of a surgical instrument adapter;

FIG. 2 is a perspective view of a plurality of the adapters of FIG. 1, illustrating the adapters attached to one another; and FIG. 3 is a perspective view of the adapter of FIG. 1 connected to a cut guide.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION

Referring to FIG. 1, adapter or connector 20 includes main block or housing 22 having a generally rectangular-shaped cross-section. Adapter 20 may be in the form of any cross-sectional shape such as to facilitate interlocking with another adapter and/or interlocking with a surgical instrument, as described further below. Adapter 20 may be formed of a polymer material or any other durable and readily disposable material.

Housing 22 includes a plurality of surfaces, such as front surface 24a, rear surface 24b, and side surfaces 26a-26d. Although the terms front, rear, and side are used to define locations for the surfaces of housing 22, these terms are not meant to limit housing 22 to such a configuration, i.e., front surface 24a may be rear surface 24a, rear surface 24b may be front surface 24b, etc., depending on a particular application.

Housing 22 also includes aperture or throughbore 28 extending therethrough from front surface 24a to rear surface 24b and oriented substantially coaxial with central axis 30 of main housing 22. Throughbore 28 provides a passageway for a fastener, as described below. Alternatively, throughbore 28 is disposed at an angle with respect to central axis 30 to provide an alternate access for a fastener extending therethrough. In another embodiment, housing 22 includes a plurality of throughbores 28.

Housing 22 further may include substantially similar recesses 32a-32c and protrusion 36. Recess 32a is formed in side surface 26a and includes first portion 33a and second portion 34a. First portion 33a is narrower than second portion 34a and recess 32a has a cross-sectional shape which is substantially identical to a cross-sectional shape defined by protrusion 36. Protrusion 36 extends from side surface 26d and includes first portion 37 and second portion 38. First portion 37 is narrower than second portion 38. First portion 37 is shaped to substantially match first portions 33 of recesses 32 and second portion 38 is shaped to substantially match second portions 34 of recesses 32. Such an arrangement allows a plurality of adapters 20 to be interlocked together, as shown in FIG. 2 and described below. Although described and shown as having generally T-shaped cross-sections, protrusion 36 and recesses 32 may have other cross-sectional shapes such as trapezoidal, L-shaped, circular, or polygonal, such that, when interlocked, protrusion 36 is slidably moveable in a recess 32 along a general direction parallel to central axis 30 but is radially fixed in recess 32 with respect to central axis 30, i.e., adapters 20 are slidably movable along the direction substantially parallel to central axis 30 but are prevented from being pulled apart along any other direction.

In operation and referring to FIG. 2, a plurality of adapters 20 can be assembled into a unitary structure. For example, adapter 20a is coupled to adapter 20b which is coupled to adapter 20c. Protrusion 36 of adapter 20a is coupled with recess 32c of adapter 20b to allow sliding movement in the general direction of central axis 30 (FIG. 1) defined by throughbore 28 of each adapter 20 and to prevent radial movement with respect to central axis 30 between adapters 20a and 20b. Similarly, protrusion 36 of adapter 20b is coupled with recess 32a of adapter 20c. Although only three adapters 20 are shown in FIG. 2, any number of adapters 20 may be coupled together in a similar manner to form a unitary structure customizable to fit any desired configuration of fastener throughbores.

In operation and referring to FIG. 3, adapter 20 is connected or otherwise assembled to a surgical instrument, such as cut guide 50, for example. Cut guide 50 includes a feature, such as cut slot 52 for guiding a saw, for example. Cut guide 50 further includes a plurality of surfaces including front surface 54a, rear surface 54b, top surface 56a, and bottom surface 56b. Although the terms front, rear, top, and bottom are used to define locations for the surfaces of cut guide 50, these terms are not meant to limit cut guide 50 to such a configuration, i.e., front surface 54a may be rear surface 54a, rear surface 54b may be front surface 54b, etc., depending on a particular application. The surgical instrument may also be a drill guide with a drilling guidance feature, a mill guide with a milling guidance feature, or an alignment guide with an alignment feature. Cut guide 50 may be similar to the cut guide described in a co-pending U.S. patent application entitled "Orthopedic Device for Securing to Tissue," obligated to be assigned to the assignee of the present application, the disclosure of which is hereby expressly incorporated herein by reference.

Top surface 56a and bottom surface 56b of cut guide 50 each may include a plurality of recesses 57 having first portion 58 and second portion 59. Recesses 57 are substantially similar in size and shape to recesses 32, described above with reference to FIGS. 1 and 2. Protrusion 36 of adapter 20 engages any one of recesses 57 depending on the desired placement of a fixation point relative to patient 70. Although not shown in FIG. 3, a plurality of adapters 20 may be attached to cut guide 50 via recesses 57 on both top surface 56a and/or bottom surface 56b. Further, a plurality of adapters 20 may also be attached to cut guide 50 via another adapter 20.

Advantageously, adapters 20 allow a customizable fixation of a surgical instrument to patient 70. Adapters 20 may be affixed to the surgical instrument in any configuration to provide optimum fixation of the surgical instrument to patient 70. For example, adapters 20 may be arranged to accommodate any bone geometry and may be slid along recesses 57, for example, of the surgical instrument to provide the fixation location. Further, multiple adapters 20 may be arranged in connection with each other to provide a fixation construct for coupling with the surgical instrument. Adapters 20 may be positioned on the surgical instrument in the most accessible location which facilitates a minimally invasive surgical procedure. Moreover, adapter 20 is formed of a material which is readily and inexpensively disposable.

In one embodiment, adapter 20 may include protrusion 36 shaped to permit swiveling movement, i.e., rotatable movement, as well as sliding movement within recess 57 of cut guide 50 to allow a surgeon to alter the angle of throughbore 28 relative to patient 70. For example, protrusion 36 may be spherical in shape and recess 57 provides a circular cross-sectional shape slot in which protrusion 36 may slide therein and rotate relative to cut guide 50, yet still able to provide adequate stable fixation of cut guide 50 to patient 70. Alternatively, adapter 20 may include a throughbore 28 disposed through main housing 22 at an angle with respect to central axis 30 to also provide an alternative angle of throughbore 28 relative to patient 70.

Alternatively, cut guide 50 may include a plurality of protrusions substantially similar to protrusions 36 for engagement with recesses 32 on adapters 20. In yet another embodiment, cut guide 50 may include a combination of recesses 57 and protrusions which are substantially similar to protrusions 36.

Adapters 20 may also be used to eliminate toggle or movement between two surgical instruments and securely attach the instruments together.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A surgical device for guiding a shaping tool to shape an anatomical structure, the device comprising:
    a surgical instrument having a guide surface, the shaping tool moveable along an extent of said guide surface;
    a first connector releasably securable to said surgical instrument in a plurality of discrete positions arranged along the extent of said guide surface; and
    a second connector alternatively releasably securable to one of said first connector and said surgical instrument, with said second connector secured to said first connector, said second connector is spaced away from the surgical instrument by the first connector, said first connector and said second connector each configured to receive a fastener for connecting said surgical instrument to the anatomical structure.

2. The surgical device of claim 1, wherein said surgical instrument comprises one of a cut guide, a mill guide, a drill guide, and an alignment guide.

3. The surgical device of claim 1, wherein said first and second connectors each comprise:
    a housing, said housing defining a central axis, a first surface, a second surface, and a plurality of side surfaces;
    a throughbore extending through said housing from said first surface to said second surface;
    a recess formed in at least one of said plurality of side surfaces; and
    a protrusion extending from another of at least one of said plurality of side surfaces.

4. The surgical device of claim 3, wherein said throughbore is substantially coaxially aligned with said central axis.

5. The surgical device of claim 3, wherein said protrusion comprises a substantially spherical shape.

6. The surgical device of claim 3, wherein said surgical instrument includes a plurality of recesses, each said recess defining a cross-sectional shape substantially identical to a cross-sectional shape defined by said protrusion of said first connector and said protrusion of said second connector, said plurality of recesses cooperating with said protrusion of said first connector and said protrusion of said second connector to allow said first connector and said second connector to be releasably secured to said surgical instrument in said plurality of discrete positions.

7. The surgical device of claim 3, wherein said surgical instrument includes a plurality of protrusions, each said protrusion defining a cross-sectional shape substantially identical to a cross-sectional shape defined by said recess of said first connector and said recess of said second connector, said plurality of protrusions cooperating with said recess of said first connector and said recess of said second connector to allow said first connector and said second connector to be releasably secured to said surgical instrument in said plurality of discrete positions.

8. The surgical device of claim 1, wherein said first connector and said second connector each comprise a polymer material.

9. The surgical device of claim 1, further comprising a third connector releasably securable to said surgical instrument in a plurality of discrete positions, said third connector configured to receive a fastener for connecting said surgical instrument to the anatomical structure.

10. The surgical device of claim 1, further comprising a second surgical instrument, said first connector and said second connector each releasably securable to said second surgical instrument in a plurality of discrete positions.

11. A surgical device usable with an anatomical structure, comprising:
   a surgical instrument;
   a fastener;
   a first connector means for cooperating with said fastener for connecting said first connector means to the anatomical structure; and
   a second connector means for connecting said surgical instrument to the anatomical structure, said second connector means disposed between said first connector means and said surgical instrument so that said first connector means and said second connector means cooperate to vary a geometrical relationship of said surgical instrument and said fastener, whereby said first and said second connector means are serially securable to said surgical instrument, with said first connector means secured to said second connector means, said first connector means is spaced away from the surgical instrument by the second connector means.

12. The surgical device of claim 11, wherein the surgical instrument comprises one of a cut guide, a mill guide, a drill guide, and an alignment guide.

13. The surgical device of claim 11, further comprising third connector means for cooperating with said fastener to connect said surgical instrument to the anatomical structure and for varying a geometrical relationship of said surgical instrument and said fastener.

14. A method of securing a surgical instrument to an anatomical structure, comprising the steps of:
   connecting a first adapter to the surgical instrument in one of a plurality of connection positions along the extent of a guiding surface of the surgical instrument;
   connecting a second adapter to the first adapter;
   fastening the surgical instrument to the anatomical structure by connecting the second adapter to the anatomical structure so that the second adapter is spaced away from the surgical instrument by the first adapter.

15. The method of claim 14, further comprising the steps of:
   evaluating a first geometrical relationship of the adapter to a guide surface of the surgical instrument and the anatomical structure;
   shaping at least a portion of the anatomical structure by moving a shaping tool along the guide surface;
   evaluating a second geometrical relationship of the adapter to the guide surface of the surgical instrument and the anatomical structure; and
   disconnecting the surgical instrument from the second adapter and reconnecting the surgical instrument to the second adapter in a different location along the guide surface to move the surgical instrument into the second geometrical relationship.

16. The method of claim 14, further comprising the step of connecting a third adapter to the surgical instrument in another of said plurality of connection positions.

17. The method of claim 14, wherein said fastening step comprises the steps of:
   orienting the adapter at a desired angle relative to the anatomical structure; and
   inserting a fastener through the adapter into the anatomical structure.

* * * * *